US009663832B2

(12) United States Patent
Ubayasena et al.

(10) Patent No.: US 9,663,832 B2
(45) Date of Patent: May 30, 2017

(54) METHOD TO DETERMINE ZYGOSITY OF THE FAD3 GENE IN CANOLA USING END-POINT TAQMAN® PCR

(71) Applicant: Dow AgroSciences LLC, Indianapolis, IN (US)

(72) Inventors: Lasantha Chandana Ubayasena, West Lafayette, IN (US); Zoe Ehlert, Saskatoon (CA); Manju Gupta, Carmel (IN); Chandra Shekara A. Channabasavaradhya, Carmel (IN)

(73) Assignee: Dow AgroSciences LLC, Indianapolis, IN (US)

( * ) Notice: Subject to any disclaimer, the term of this patent is extended or adjusted under 35 U.S.C. 154(b) by 822 days.

(21) Appl. No.: 13/656,270

(22) Filed: Oct. 19, 2012

(65) Prior Publication Data

US 2013/0102002 A1    Apr. 25, 2013

Related U.S. Application Data

(60) Provisional application No. 61/550,170, filed on Oct. 21, 2011.

(51) Int. Cl.
*C12Q 1/68* (2006.01)
(52) U.S. Cl.
CPC ..... *C12Q 1/6895* (2013.01); *C12Q 2600/156* (2013.01)

(58) Field of Classification Search
None
See application file for complete search history.

(56) References Cited

U.S. PATENT DOCUMENTS

| 7,081,564 | B2* | 7/2006 | Somers et al. | 800/281 |
|---|---|---|---|---|
| 2006/0248611 | A1* | 11/2006 | Hu et al. | 800/281 |
| 2008/0227663 | A1 | 9/2008 | Tisone et al. | |
| 2011/0151441 | A1 | 6/2011 | Chen et al. | |
| 2014/0007267 | A1* | 1/2014 | Cole | A01H 5/10 800/260 |

FOREIGN PATENT DOCUMENTS

| CN | 101591697 A | 12/2009 |
|---|---|---|
| CN | 101591697 A | 12/2009 |
| WO | WO 2004/072259 A2 | 8/2004 |
| WO | WO 2011/060946 A1 | 5/2011 |
| WO | WO 2011/075648 | 6/2011 |

OTHER PUBLICATIONS

Schmidt et al. (J Agric Food Chem 2006, 54:1158-1165).*
Lowe et al. (Nucleic Acids Research, 1990, 18(7):1757-1761).*
Ferreira, Eduardo C. et al., Alternative PCR protocol using a single primer set for assessing DNA quality in several tissues from a large variety of mammalian species living in areas endemic for leishmaniasis, Mem Inst Oswaldo Cruz, Rio de Janeiro, vol. 105(7): 895-898, Nov. 2010.
Noelle A. Barkley, et al., "A real-time PCR genotyping assay to detect FAD2A SNPs in peanuts (*Arachis hypogaea* L.)", Electronic Journal of Biotechnology, vol. 14, No. 1, Oct. 10, 2001 (Oct. 10, 2001), XP55187674, ISSN: 0717-3458, DOI: 10.2225/vol14-issue 1-full text-12, abstract, p. 5, paragraph 2.
Noelle A. Barkley, et al., "A real-time PCR genotyping assay to detect FAD2A SNPs in peanuts (Arachis hypogaea L.)", Electronic Journal of Biotechnology, vol. 14, No. 1, Oct. 10, 2001 (Oct. 10, 2001), XP55187674, ISSN: 0717-3458, DOI: 10.2225/vol14-issue1-full text-12, abstract, p. 5, paragraph 2.
Giancola, Sandra, et al., "Utilization of the three high-throughput SNP genotyping methods, the Good assay, Amplifluor and TaqMan, in diploid and polyploid plants", Theoretical and Applied Genetics, Feb. 2, 2006, vol. 112, Issue 6, pp. 1115-1124.
Qiuying Huang, et al., "Multiplex Flourescence Melting Curve Analysis for Mutation Detection with Dual-Labeled, Self-Quenched Probes", PLOS One, vol. 6, No. 4, Apr. 28, 2011 (Apr. 28, 2011), p. e19206, XP055021038, ISSN: 1932-6203, DOI: 10.1371/journal.pone.0019206, abstract, figures 1-2, 5.
EPO, Extended European Search Report, EP 12 84 1612, Dow AgroSciences LLC, Jun. 1, 2015.
WIPO, International Preliminary Report on Patentability, PCT/US2012/062000, Dow AgroSciences LLC, Apr. 22, 2014.
Ferreira, Eduardo C. et al., Alternative PCR protocol using a single primer set for assessing DNA quality in several issues from a large variety of mammalian species living in areas endemic for leishmaniasis, Mem Inst Oswaldo Cruz, Rio de Janeiro, vol. 105(7): 895-898, Nov. 2010.

* cited by examiner

*Primary Examiner* — Stephanie K Mummert
(74) *Attorney, Agent, or Firm* — Marcia I. Rosenfeld; Faegre Baker Daniels LLP

(57) ABSTRACT

The subject disclosure relates in part to endpoint TaqMan® PCR assays for the detection and high throughput zygosity analysis of the fad-3c gene in canola. The subject disclosure further relates, in part, to the use of wild type DNA as a reference for use in determining zygosity. These and other related procedures can be used to uniquely identify the zygosity and variety of canola lines comprising the subject gene. The subject disclosure also provides related kits for determining zygosity from a sample of a canola plant or seed, for example.

13 Claims, 2 Drawing Sheets

Exon 6
ATCTTTGTAATGTGGTTGGACGCTGTCACGTACTTGCATCATCATCGTCACGATGATAAG
Intron 6
CTGCCTTGGTACAGAGGCAAGGTAAGTAGATCAGCATTATTTATAAGAAGCAATAATGAT
Exon 7
TAGTAGTTGAATAATCTGAATTTTTGATGTTTTTGTACAATAATAGGAATGGAGTTATTTAC
Fed 2c mutation (G to A)
GTGGAGGATTAACAACTGTTGATAGAGATTACGGGATCTTCAACAACATTCATCACGATA
TTGGAACTCACGTGATCCATCATCTTTTCCACAAATCCC

FIG. 1

SEQUENCE LISTING

<160> NUMBER OF SEQ ID NOS: 5

<210> SEQ ID NO 1
<211> LENGTH: 282
<212> TYPE: DNA
<213> ORGANISM: artificial sequence
<220> FEATURE:
<223> OTHER INFORMATION: section of canola fad-3c gene sequence

<400> SEQUENCE: 1
atctttgtaa tgtggttgga cgctgtcacg tacttgcatc atcatggtca cgatgataag    60

```
ctgccttggt acagaggcaa ggtaagtaga tcagcattat ttataagaag caataatgat    120
tagtagttga ataatctgaa tttttgatgt ttttgtacaa taataggaat ggagttattt    180
acgtggagga ttaacaactg ttgatagaga ttacgggatc ttcaacaaca ttcatcacga    240
tattggaact cacgtgatcc atcatctttt cccacaaatc cc                      282

<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
acgatgataa gctgccttgg t                                              21

<210> SEQ ID NO 3
<211> LENGTH: 24
<212> TYPE: DNA
<213> ORGANISM: artificial sequence
<220> FEATURE:
<223> OTHER INFORMATION: primer

<400> SEQUENCE: 3
tcaacagttg ttaatcctcc acgt                                           24

<210> SEQ ID NO 4
<211> LENGTH: 16
<212> TYPE: DNA
<213> ORGANISM: Artificial sequence
<220> FEATURE:
<223> OTHER INFORMATION: probe

<400> SEQUENCE: 4
cagaggcaag ataagt                                                    16

<210> SEQ ID NO 5
<211> LENGTH: 17
<212> TYPE: DNA
<213> ORGANISM: artificial sequence
<220> FEATURE:
<223> OTHER INFORMATION: probe

<400> SEQUENCE: 5
acagaggcaa ggtaagt                                                   17
```

METHOD TO DETERMINE ZYGOSITY OF THE FAD3 GENE IN CANOLA USING END-POINT TAQMAN® PCR

CROSS-REFERENCE TO RELATED APPLICATION

This application claims priority to U.S. Provisional Application No. 61/550,170, filed Oct. 21, 2011, which is herein incorporated by reference in its entirety.

BACKGROUND OF THE DISCLOSURE

The genus *Brassica* includes canola, one of the world's most important oilseed crops, and an important oilseed crop grown in temperate geographies. Canola has been traditionally characterized as *Brassica napus* L. (a species derived as a result of inter-specific crosses of *Brassica rapa* and *Brassica oleracea*) in which erucic acid and glucosinolates have been eliminated or significantly reduced through conventional breeding. The majority of canola oil is in the form of vegetable oils produced for human consumption. There is also a growing market for the use of canola oil in industrial applications.

The genus *Brassica* is comprised of three diploid species each which possess a unique genome which is labeled as either the A genome, B genome, or C genome. *Brassica rapa* plants possess a diploid A genome. *Brassica nigra* plants possess a diploid B genome. *Brassica oleracea*, plants posses a diploid C genome. Hybrids of these species can be produced via crossing between two of the diploid species. Canola is an amphidiploid species considered to have arisen from the hybridization of *Brassica oleracea*, having a diploid C genome, and *Brassica rapa*, having a diploid A genome. Cytogenetic investigation revealed the AA and CC genomes show a degree of relatedness, being partially homologous to one another and thought to have been derived from a common ancestor genome (Prakash and Hinata, 1980). Although technically classified as diploids, the genomes of both progenitor species contain a high percentage of regions duplicative of one another (Song et al, 1991). Genetic analysis revealed that the AA genome of *Brassica rapa* contributed ten chromosomes to *Brassica napus*, while *Brassica oleracea* contributed nine chromosomes from its CC genome as the maternal donor (Song et al, 1992).

The quality of edible and industrial oil derived from a particular variety of canola seed is determined by its constituent fatty acids, as the type and amount of fatty acid unsaturation have implications for both dietary and industrial applications. Conventional canola oil contains about 60% oleic acid (C18:1), 20% linoleic acid (C18:2) and 10% linolenic acid (18:3). The levels of polyunsaturated linolenic acid typical of conventional canola are undesirable as the oil is easily oxidized, the rate of oxidation being affected by several factors, including the presence of oxygen, exposure to light and heat, and the presence of native or added antioxidants and pro-oxidants in the oil. Oxidation causes off-flavors and rancidity of as a result of repeated frying (induced oxidation) or storage for a prolonged period (auto-oxidation). Oxidation may also alter the lubricative and viscous properties of canola oil.

Canola oil profiles which exhibit reduced levels of polyunsaturated fatty acids and increased levels of monounsaturated oleic acid relative to conventional canola oil are associated with higher oxidative stability. The susceptibility of individual fatty acids to oxidation is dependent on their degree of unsaturation. Thus, the rate of oxidation of linolenic acid, which possesses three carbon-carbon double bonds, is 25 times that of oleic acid, which has only one carbon-carbon double bond, and 2 times that of linoleic acid, which has two carbon-carbon double bonds. Linoleic and linolenic acids also have the most impact on flavor and odor because they readily form hydroperoxides. High oleic oil (.gtoreq.70% oleic) is less susceptible to oxidation during storage, frying and refining, and can be heated to a higher temperature without smoking, making it more suitable as cooking oil.

The quality of canola oil is determined by its constituent fatty acids such as oleic acid (C18:1), linoleic acid (C18:2) and linolenic acid (C18:3). Most canola cultivars normally produce oil with about 55-65% oleic acid and 8-12% linolenic acid. High concentrations of linolenic acid lead to oil instability and off-type flavor, while high levels of oleic acid increase oxidative stability and nutritional value of oil. Therefore, development of canola cultivars with increased oleic acid and reduced linolenic acid is highly desirable for canola oil quality.

Two loci were identified and their genomic location mapped from a canola cultivar which possesses increased oleic acid and reduced linolenic acid quantities. One locus has a major effect, and the second locus has a minor effect on production of increased oleic acid and reduced linoleic acid. The major locus for high oleic acid (C18:1) was determined to be the fatty acid desaturase-2 (fad-2) gene and it is located on linkage group, N5. The second locus is located on linkage group N1. One major Quantitative Trait Loci (QTL) for linolenic acid (C18:3) is the fatty acid desaturase-3 gene of the genome C (fad-3c) and it is located on linkage group N14. The second major QTL resides on the N4 linkage group and is the fatty acid desaturase-3 gene of the genome A (fad-3a). Genomic sequences of the fad-2 and fad-3c genes were amplified and sequenced from both an ethyl methanesulfonate (EMS)-induced mutant and a wild-type canola cultivar. A comparison of the mutant and wild-type allele sequences of the fad-2 and fad-3c genes revealed single nucleotide polymorphisms (SNPs) in the genes from the EMS mutated plants. Based on the sequence differences between the mutant and wild-type alleles, two SNP markers, corresponding to the fad-2 and fad-3c gene mutations, were developed. (Hu et al., 2006).

Current methods for producing $F_1$ hybrid *Brassica* seeds have limitations in terms of cost and seed purity. Generally, these methods require stable, sib-incompatible and self-incompatible, nearly homozygous parental breeding lines, which parental breeding lines are available only after repeated selfing to generate inbred lines. Furthermore, inbreeding to develop and maintain the parental lines is accomplished by labor intensive techniques, such as bud pollination, since *Brassica* hybrid seed production systems based on self-incompatible traits must utilize strongly self-incompatible plants. Environmental conditions during the breeding process, such as temperature and moisture, typically affect plant lipid metabolism, thus also affecting the content level of fatty acids (Harwood, 1999). Environmental variability therefore makes the phenotypic selection of plants less reliable. Deng and Scarth (1998) found that increase in post-flowering temperature significantly reduced the levels of C18:3 and increased C18:1. Similar results were reported in other studies (Yermanos and Goodin, 1965; Canvin, 1965).

Breeding for low linolenic varieties is particularly challenging since C18:3 content is a multi-gene trait and inherited in a recessive manner with a relatively low heritability.

Genetic analysis of a population derived from the cross between "Stellar" (having a low C18:3 content (3%)) and "Drakkar" (having a "conventional" C18:3 level (9-10%)) indicated that the low C18:3 trait was controlled by two major loci with additive effects designated L1 and L2 (Jourdren et al., 1996b). These two major loci controlling C18:3 content were found to correspond to two fad-3 (fatty acid desaturase-3) genes; one located on the A genome (originating from Brassica rapa) and the other on the C genome (originating from Brassica olecera) (Jourdren et al., 1996; Barret et al., 1999).

Traits that are continuously varying due to genetic (additive, dominance, and epistatic) and environmental influences are commonly referred to as "quantitative traits." Quantitative traits may be distinguished from "qualitative" or "discrete" traits on the basis of two factors: environmental influences on gene expression that produce a continuous distribution of phenotypes; and the complex segregation pattern produced by multigenic inheritance. The identification of one or more regions of the genome linked to the expression of a quantitative trait led to the discovery of Quantitative Trait Loci ("QTL"). Thormann et al. (1996) mapped two QTL that explained 60% of the variance for the linolenic content, while Somers et al. (1998) identified three QTL that collectively explained 51% of the phenotypic variation of C18:3 content. A three-locus additive model was also reported by Chen and Beversdorf (1990). Rucker and Robbelen (1996) indicated that several minor genes are most likely involved in the desaturation step.

Heritability for C18:3 content was estimated to be 26-59% (Kondra and Thomas, 1975) (where the variability of heritability is a function of genetics as opposed to environmental factors). Complexity of the inheritance of linolenic acid may be due to the fact that linolenic acid can be synthesized either from the desaturation of C18:2 or the elongation of C16:3 (Thompson, 1983).

In contrast to linolenic acid, inheritance of oleic acid is less complex, and the heritability of oleic acid is relatively high. It is reported that high oleic acid content is controlled by a major locus called fad-2 (fatty acid desaturase 2) gene which encodes the enzyme responsible for the desaturation of oleic acid to linoleic acid (C18:2) (Tanhuanpaa et al., 1998; Schierholt et al., 2001). All of the functional gene copies of the fad-2 gene that have been reported and mapped to date are located on the A-genome-originated linkage group N5 (Scheffler et al., 1997; Schierholt et al., 2000). Chen and Beversdorf (1990) reported that the accumulation of oleic acid was controlled by at two segregation genetic systems, one acting on chain elongation and the other involving desaturation. Heritability for C18:1 content was estimated to be 53% to 78% (Kondra and Thomas 1975) and 94% (Schierholt and Becker, 1999), respectively. Due to the higher heritability, the expression of C18:1 content is environmentally less affected and relatively stable (Schierholt and Becker, 1999).

In Nexera™ canola germplasm, 1 to 2 genes are found to control C18:1 content and at least 3 genes are involved in C18:3 expression (Nexera™ is a trademark of Dow AgroSciences, LLC). In segregating progenies, the distribution of seed C18:3 content is continuous, thereby making it difficult to identify genotypic classes with desirable C18:3 levels. In addition, there is a low correlation in fatty acid content between greenhouse (GH) and field grown plants, further making it challenging to reliably select GH plants with desirable levels of C18:3.

Various methods can be used to detect the presence of a specific gene in a sample of plant tissue. One example is the Pyrosequencing technique as described by Winge (Innov. Pharma. Tech. 00:18-24, 2000). In this method an oligonucleotide is designed that overlaps the inserted DNA sequence and the genomic DNA adjacent thereto. thereto The oligonucleotide is hybridized to a single-stranded PCR product (an "amplicon") from the region of interest (i.e., one primer in the inserted sequence and one in the flanking genomic sequence) and incubated in the presence of a DNA polymerase, ATP, sulfurylase, luciferase, apyrase, adenosine 5' phosphosulfate and luciferin. dNTPs are added individually and the incorporation results in a light signal that is measured. A light signal indicates the presence of the transgene insert/flanking sequence due to successful amplification, hybridization, and single or multi-base extension. (This technique is usually used for initial sequencing, not for detection of a specific gene when it is known.)

Fluorescence Polarization is another method that can be used to detect an amplicon. Following this method, an oligonucleotide is designed to overlap the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Molecular Beacons have been described for use in sequence detection. Briefly, molecular beacons comprise a FRET (fluorescence resonance energy transfer) oligonucleotide probe which may be designed such that the FRET probe overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal indicates the presence of the flanking genomic/transgene insert sequence due to successful amplification and hybridization.

Hydrolysis probe assays, also known as TaqMan® PCR (TaqMan® is a registered trademark of Roche Molecular Systems, Inc.), provide a method of detecting and quantifying the presence of a DNA sequence. Briefly, TaqMan® PCR utilizes a FRET oligonucleotide probe which is designed to have a portion of the oligo within the transgene and another portion of the oligo within the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe, and subsequent digestion during the PCR amplification stage due to 5' exonuclease activity of the Taq polymerase, results in cleavage and release of the fluorescent moiety away from the quenching moiety on the FRET probe. A fluorescent signal indicates the presence of the flanking/transgene insert sequence due to successful hybridization and amplification.

Molecular markers are also useful for sequence specific identification of DNA. Molecular marker selection is based on genotypes and is therefore independent from environment effects. Molecular markers help to alleviate the problem of the unreliable selection of plants in the greenhouse attributable to the low correlation in fatty acid content between greenhouse grown plants and field grown plants. Significantly, molecular markers tightly linked to the genes controlling C18:1 and C18:3 content can facilitate early selection of plants carrying genes for high C18:1 and low C18:3. Marker-assisted selection at early stage can help to save greenhouse space, improve the efficiency of greenhouse use, and reduce breeding workload in the field.

More generally, molecular markers have advantages over morphological markers in that: molecular markers can be highly polymorphic while morphological markers are strictly phenotype dependent; morphological markers may interfere in the scoring of certain quantitative phenotypes while molecular markers exhibit a 1:1 relationship between genotype and phenotype (thus allowing the unambiguous scoring of all possible genotypes for a given locus); and epistatic interactions tend to limit the number of morphological markers useful in a population, while molecular markers do not interact epistatically.

Different types of molecular markers such as RAPD (random-amplified polymorphic DNA) markers (Tanhuanpaa et al., 1995; Hu et al., 1995; Rajcan et al., 1999; Jourdren et al., 1996), RFLP (restriction fragment length polymorphism) markers (Thormann et al., 1996) and SCAR (sequence-characterized amplified region) markers (Hu et al, 1999) have been identified to be associated with low C18:3 levels in Brassica napus. Molecular markers have also been identified for high C18:1 content. A RAPD marker was identified to be linked to the QTL affecting oleic acid concentration in spring turnip rape (*B. rapa* ssp. *oleifera*) and was later converted into a SCAR marker (Tanhuanpaa et al., 1996). Schierholt et al. (2000) identified three AFLP (amplified fragment length polymorphism) markers linked to a high oleic acid mutation in winter oilseed rape (*B. napus* L.). Tanhuanpaa et al. (1998) developed an allele-specific PCR marker for oleic acid by comparing the wild-type and high-oleic allele of the fad-2 gene locus in spring turnip rape (*B. rapa* ssp. *oleifera*). However, most of these markers are low-throughput markers such as RAPD, AFLP and RFLP and are not suitable for large scale screening through automation.

BRIEF SUMMARY OF THE DISCLOSURE

The subject disclosure relates in part to endpoint TaqMan® PCR assays for the detection, and high throughput zygosity analysis, of the fad-3c gene in canola. The subject disclosure further relates, in part, to the use of wild-type fad-3c gene in canola as a reference for use in determining zygosity. These and other related procedures can be used to uniquely identify the zygosity and variety of canola lines comprising the subject gene.

The subject disclosure also provides related kits for determining the zygosity and variety from a sample (of canola, for example).

Thus, an embodiment of the subject disclosure relates to TaqMan® PCR, a flexible platform for high throughput zygosity and breeding analysis. Utilization of the end-point TaqMan® PCR application presented herewith this disclosure provides a reliable, accurate, and high throughput application for fad-3c zygosity and breeding analysis of canola.

BRIEF DESCRIPTION OF THE FIGURES

FIG. 1. is a section of fad-3c gene sequence (SEQ ID NO:1) illustrating the position of the fad-3c mutation identified by Hu et al. (2006) (arrow). Intron 6 is in lighter colored text and a second polymorphism is indicated with an asterisk.

BRIEF DESCRIPTION OF THE SEQUENCES

Figure 2:
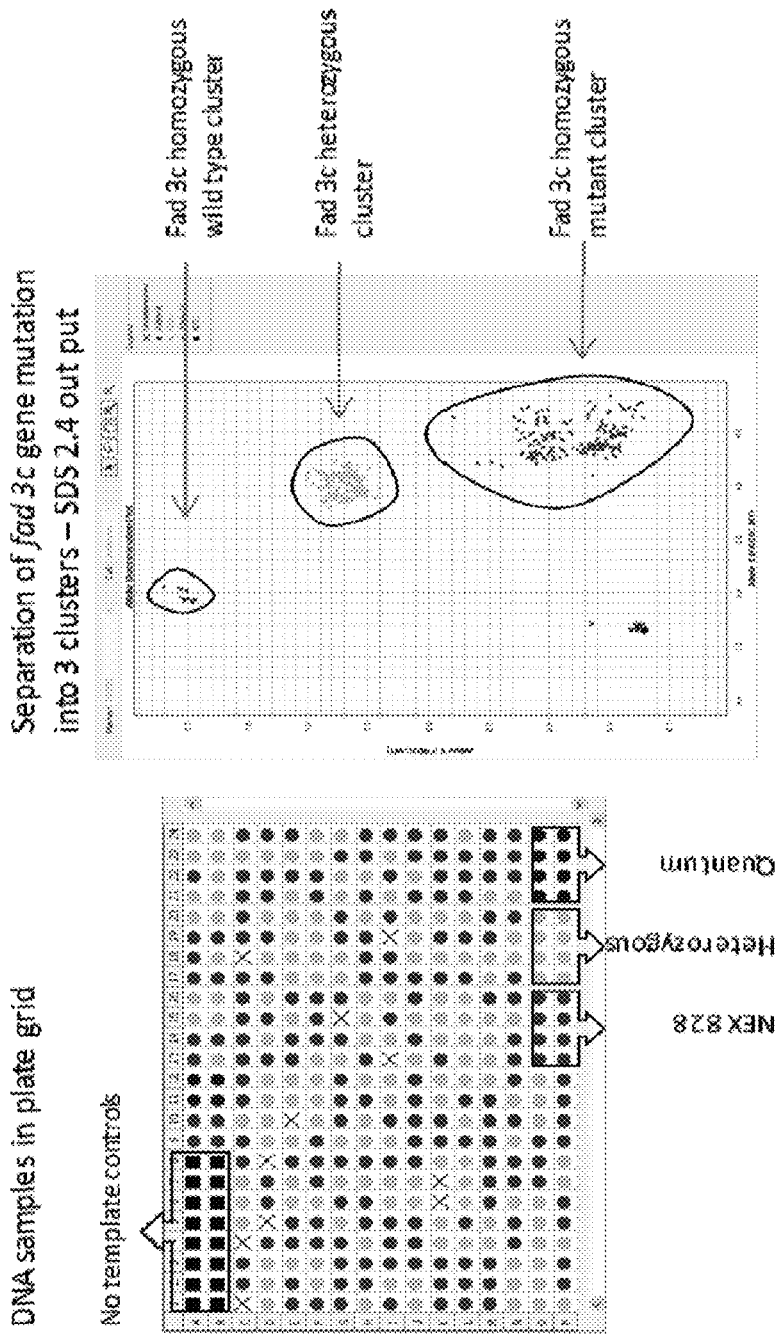
FIG. 2. is an example of zygosity analysis results (of canola), showing three fad-3c genotypes following an end point TaqMan® assay (results generated using SDS 2.4 software available through Applied Biosystems, Foster City, Calif., USA).

SEQ ID NO:1 provides a section of the fad-3c gene sequence illustrating the position of the fad-3c mutation.
SEQ ID NO:2 provides forward primer D-CL-FAD3C-F (which binds flanking genomic sequence).
SEQ ID NO:3 provides reverse primer D-CL-FAD3C-R2 (which binds insertion sequence).
SEQ ID NO:4 provides probe D-CL-FAD3C-FAM for preferential binding of mutated fad-3c gene having a G to A single nucleotide polymorphism.
SEQ ID NO:5 provides probe D-CL-FAD3C-VIC for detection of wild type fad-3c gene.

DETAILED DESCRIPTION OF THE DISCLOSURE

The subject disclosure relates in part to endpoint TaqMan® PCR assays for the detection and high throughput zygosity analysis of the fad-3c gene in canola. The subject disclosure further relates, in part, to the use of wild-type fad-3c gene in canola as a reference for use in determining zygosity. These and other related procedures can be used to uniquely identify the zygosity and variety of canola lines comprising the subject gene. The subject disclosure also provides related kits for determining the zygosity and variety from a sample (of canola, for example). Thus, an embodiment of the subject disclosure relates to TaqMan® PCR, a flexible platform for high throughput zygosity and breeding analysis. Utilization of the end-point TaqMan® PCR application presented herewith this disclosure provides a reliable, accurate, and high throughput application for fad-3c zygosity and breeding analysis of canola.

Novel assays of the subject invention were developed based in part on a single nucleotide polymorphism (SNP) mutation of the fad-3c allele reported by Hu et al. (2006). The assay utilizes two primer regions and two MGB probes to detect mutant and wild type fad-3c alleles (see Table 1). TaqMan® primers and probes to detect this SNP mutation were designed in part by Primer express software (Applied Biosystems, Austin, Tex.) using the fad-3c gene sequences. This new fad-3c TaqMan® assay was validated using DNA extracted from canola plants which are homozygous, hemizygous and wild type (no mutation) for the fad-3c gene. The fad-3c TaqMan® assay was also optimized for performance in part with the Applied Biosystems 7900HT Real-Time PCR system on both the 96 or 384 well formats using fast PCR thermal cycling conditions

TABLE 1

Primer and probe sequences used in the fad-3c TaqMan ® assay

| SEQ ID NO: | Name | Description | Sequence (5'-3') |
|---|---|---|---|
| SEQ ID NO: 2 | D-CL-FAD3c-F | Forward primer | ACGATGATAAGCTGCCTTGGT |
| SEQ ID NO: 3 | D-CL-FAD3c-R | Reverse primer | TCAACAGTTGTTAATCCTCCACGT |
| SEQ ID NO: 4 | D-CL-FAD3c-FAM | Probe to detect fad-3c mutant | 6FAM-CAGAGGCAAGATAAGT-MGB |
| SEQ ID NO: 5 | D-CL-FAD3c-VIC | Probe to detect fad-3c wild type | VIC-ACAGAGGCAAGGTAAGT-MGB |

NEX828 and Quantum leaf samples were used in the assay. DNA from canola breeding populations were used to validate this assay.

Aspects of the subject disclosure include methods of designing and/or producing diagnostic nucleic acid molecules exemplified and/or suggested herein. Specific TaqMan® primers and probe were designed, as detailed herein, in part according to the DNA sequences located at, or in proximity upstream or downstream to, the specific SNPs identified herein in the fad-3c gene.

Thus, in some embodiments, this disclosure relates to determining zygosity of canola oil producing plants. The subject disclosure relates in part to detecting the presence of SNPs identified herein, in order to determine whether progeny of a sexual cross contain the SNPs of interest, and the zygosity of the progeny. In addition, methods for detecting zygosity are included and are helpful, for example, for complying with regulations requiring the pre-market approval and labeling of foods derived from recombinant crop plants.

The subject disclosure relates in part to a fluorescence-based endpoint TaqMan® PCR assay utilizing the endogenous, non-mutant fad-3c gene as a control for high-throughput zygosity analysis of canola plants.

The subject disclosure also relates in part to the development of a biplex endpoint TaqMan® PCR for canola zygosity analysis. Further, the subject disclosure relates in part to the development of canola fad-3c gene breeding test kits.

In general, endpoint TaqMan® assays are based on a plus/minus strategy, by which a "plus" signifies the sample is positive for the assayed gene and a "minus" signifies the sample is negative for the assayed gene. These assays typically utilize one set of oligonucleotide primers and two oligonucleotide probes, one probe preferentially hybridizing the mutated fad-3c SNP and the other probe preferentially hybridizing the wild-type fad-3c sequence, respectively.

Advantages associated with the subject disclosure include its decreased reliance on DNA quality and quantity. Further, the subject disclosure does not require a lengthy initial denaturing step which, if not handled properly, can often render other SNP detection assays unsuccessful. Additionally, the subject disclosure is provides a method to efficiently analyze large numbers of canola samples in a high-throughput manner within a commercial setting. Another advantage of the subject disclosure is time savings. The subject Endpoint TaqMan® analysis for canola zygosity and breeding analysis offers advantages over other application formats, particularly when analyzing large numbers of samples.

This disclosure relates in part to plant breeding analysis. This disclosure includes novel detection of methods for SNPs in canola plants that affect oleic and linolenic acid levels in the subject plants.

Further, it may be possible to detect the presence of the subject SNPs by other known nucleic acid detection methods, such as PCR or DNA hybridization using the nucleic acid probes described herein. Event-specific PCR assays are discussed herein. (See also Windels et al. (Med. Fac. Landbouww, Univ. Gent 64/5b:459462, 1999.)

As used herein, the term "progeny" denotes the offspring of any generation of a parent plant.

Detection techniques of the subject disclosure are especially useful in conjunction with plant breeding, for example, to determine zygosity of progeny plants after a parent plant comprising a SNP of interest is crossed with another plant. The subject application and methods benefit canola breeding programs as well as quality control processes. PCR detection kits for canola lines, using the methods and assays disclosed herein can now be made and used. Further, the subject disclosure may benefit product registration and product stewardship.

A canola plant comprising desired fad-3c genetic composition can be bred by first sexually crossing a first parental canola plant consisting of a canola plant grown from seed of any one of the lines referred to herein, and a second parental canola plant, thereby producing a plurality of first progeny plants; and then selecting a first progeny plant possessing desired fad-3c genes as disclosed by the subject disclosure; and selfing the first progeny plant, thereby producing a plurality of second progeny plants; and then selecting from the second progeny plants a plant that possesses desired fad-3c genes according to the subject disclosure. These steps can further include the back-crossing of the first progeny plant or the second progeny plant to the second parental canola plant or a third parental canola plant. A canola crop comprising canola seeds of the subject disclosure, or progeny thereof, can then be planted.

This disclosure further includes processes of making crosses using canola plant comprising the desired fad-3c genetic composition as at least one parent. For example, the subject disclosure includes an $F_1$ hybrid plant having as one or both parents any of the canola plant comprising the desired fad-3c genetic composition. Also within the subject disclosure is seed produced by such $F_1$ hybrids. This disclosure includes a method for identifying an $F_1$ hybrid seed by crossing an exemplified plant with a different (e.g. in-bred parent) plant and harvesting and assaying the resultant hybrid seed, using the method of the subject disclosure. The canola plants that are used to produce the $F_1$ hybrid may be either a female parent or a male parent.

It is also to be understood that transgenic plants may be produced to contain the fad-3c genes disclosed herein. Additionally, transgenic plants comprising the fad-3c gene characteristics disclosed herein may be mated with a plant comprising a different genetic composition, thereby producing offspring containing independently segregating exogenous genes. Selfing of appropriate progeny can produce plants that are homozygous for the added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply introgressed, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent. The method of the subject disclosure provides a high-throughput, fluorescence-based endpoint TaqMan® PCR assay to detect the fad-3c transgene in progeny plants and to determine the zygosity level of progeny plants.

The methods of the present disclosure, for example the oligonucleotide primers and probes, can be used for marker assisted breeding (MAB) methods. The methods of the present disclosure, for example the oligonucleotide primers and probes, can be used with related assays Amplified Fragment Length Polymorphism assays (AFLP) Restrictive Fragment Length Polymorphism assays (RFLP) Random Amplified Polymorphism DNA assays (RAPD)) that identify genetically linked agronomically useful traits by the detection of SNPs or Simple Sequence Repeats (SSRs), using publicly available protocols that are known in the art. The SNPs disclosed herein can be tracked in the progeny of a cross with a canola plant of the subject disclosure (or progeny thereof and any other canola cultivar or variety) using the MAB methods. DNA molecules can be used as markers for this trait, and MAB methods that are well known in the art can be used to track the SNPs in canola plants where at least one canola plant of the subject disclosure, or progeny thereof, was a parent or ancestor. The methods of the present disclosure can be used to identify any canola variety having the subject SNPs disclosed herein.

Methods of the subject disclosure include a method of producing a canola plant comprising a combination of the SNPs identified herein, wherein said method comprises breeding with a plant of the subject disclosure. More specifically, said methods can comprise crossing two plants of the subject disclosure, or one plant of the subject disclosure and any other plant. Exemplary methods may further comprise selecting progeny of said cross by analyzing said progeny for a SNP of the subject disclosure, detectable according to the subject disclosure. For example, the subject disclosure can be used to track the zygosity of canola plants through breeding cycles with plants comprising other desirable traits, such as agronomic traits such as those tested herein in various Examples. Plants comprising the subject SNPs and the desired traits may also be detected, identified, selected, and quickly used in further rounds of breeding, for example. The subject SNPs/traits can also be combined through breeding, and tracked according to the subject disclosure, with other traits, for example possible insect resistant trait(s) and/or herbicide tolerance traits. One embodiment of the latter is a plant comprising one or more of the subject SNPs combined with a gene encoding resistance to a herbicide such as glyphosate.

In some embodiments, the present disclosure includes DNA sequences that comprise a contiguous fragment useful as primer sequences for the production of an amplicon product diagnostic for one or more of the fad-3c canola plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a portion of DNA sequences identified herein, or complements thereof. Such sequences may be useful as DNA primers in DNA amplification methods. The amplicons produced using these primers may be diagnostic for any combination and zygosity of fad-3c canola varieties referred to herein. Therefore, the disclosure also includes the amplicons produced by such DNA primers and homologous primers.

In still further embodiments, the subject disclosure includes methods of producing fad-3c SNPs of the subject disclosure, wherein said method comprises the steps of: (a) sexually crossing a first parental canola line comprising one of the SNPs disclosed herein and conferring one of the oleic and/or linolenic acid traits disclosed here) and a second parental canola line (that lacks these SNPs) thereby producing a plurality of progeny plants; and (b) selecting a progeny plant by the use of molecular markers. Such methods may optionally comprise the further step of back-crossing the progeny plant to the second parental canola line to produce a true-breeding or homozygous canola plant that comprises said fad-3c traits.

According to another aspect of the disclosure, methods of determining the zygosity of progeny of a cross with said fad-3c canola plants is provided. Said methods can comprise contacting a sample, comprising canola DNA, with a primer set of the subject disclosure. Said primers, when used in a nucleic-acid amplification reaction with genomic DNA from at least one of said fad-3c canola plants, produces a first amplicon that is diagnostic for at least one of said canola SNPs or wild type genes. Such methods further comprise performing a nucleic acid amplification reaction, thereby producing the first amplicon and detecting the first amplicon with probes specific for the SNPs of the fad-3c disclosed herein and the wild type genes. The methods further comprise performing allelic discrimination melting applications of the amplicons having the disclosed probes annealed thereto, and comparing the relative florescence of the probes used in the allelic discrimination melting application. The relative florescence of the probes indicates whether the sample contains the SNP of interest, and if so, whether the sample is heterozygous or homozygous for the SNP.

DNA detection kits can be developed using the compositions disclosed herein, in conjunction with methods well known in the art of DNA detection. The kits are useful for identification of the subject canola SNPs in a sample and can be applied to methods for breeding canola plants containing this DNA. The kits contain DNA sequences homologous or complementary to the amplicons, for example, disclosed herein. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present disclosure, to a strand of genomic DNA from one of said canola plants comprising fad-3c genes of interest, whether from a canola plant or from a sample that includes DNA from the event. Probes according to the present disclosure include not only deoxyribonucleic or ribonucleic acids but also polyamides and other probe materials that bind specifically to a target DNA sequence and can be used to detect the presence of that target DNA sequence.

Specific probes were designed comprising a fluorescent reporter (fluorophore) and a quencher that hybridizes to the target DNA between the PCR primers. The fluorophore molecule is added to an oligonucleotide probe during the synthesis of the oligonucleotide probe thereby labeling the oligonucleotide probe. Other molecules can be added to oligonucleotide probe, such as a quencher molecule. The addition of these molecules to an oligonucleotide probe does not impair the function of the oligonucleotide probe when hybridizing to single stranded DNA and producing a new strand of DNA via an amplification process.

Numerous fluorophores have been developed that excite at specific wavelengths and are known in the art. Excitation of the fluorophore results in the release of a fluorescent signal by the fluorophore which can be quenched by a quencher located in close proximity to the fluorophore. When the quencher is disassociated from the fluorophore, the fluorescent signal is no longer quenched and accumulation of the fluorescent signal, which is directly correlated with the amount of target DNA, can be detected in real-time with an automated fluorometer. The fluorophores may be used in combination, wherein the excitation and emission spectra are significantly differ as to allow multiple detection of two or more fluorophores. Some preferred embodiments of fluorophores include; a HEX fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, or a ROX fluorescent dye. One preferred embodiment of a fluorophore for use with the method consisting of a homogeneous assay detection system for a PCR process using FRET of the subject invention includes a FAM fluorescent dye of a JOE fluorescent dye.

Quenchers have been developed to quench fluorophores at a specific wavelength and are known in the art. When the quencher is located in close approximation to the fluorophore, the fluorophore transfers energy to the quencher. The quencher transfer this energy and returns to a native ground state through emissive decay or nonradiatively. In nonradiative or dark decay, the energy transferred from the fluorophore is given off as molecular vibrations. Selection of a quencher considers qualities such as low background fluorescence, high sensitivity, and maximal spectral overlap to provide a quencher that can enable a wider use of fluorophores. Some preferred embodiments of quenchers include; Dabcyl quenchers, Tamra quenchers, Qxl quencher, Iowa black FQ quencher, Iowa black RQ quencher, or an IR Dye QC-1 quencher. An especially preferred embodiment of a quencher would include an Blackhole quencher labeled on an oligonucleotide primer which is designed antisense to the FAM labeled oligonucleotide.

"Primers" are isolated/synthesized nucleic acids that are annealed to a complementary target DNA strand by nucleic acid hybridization, thereby forming a hybrid between the primer and the target DNA strand and then extended along the target DNA strand by a polymerase, e.g., a DNA polymerase. Primer pairs of the present disclosure refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present disclosure have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the DNA sequences upstream and downstream of the SNPs disclosed herein can be used to confirm (and, if necessary, to correct) the disclosed sequences by conventional methods, e.g., by re-cloning and sequencing such sequences.

The nucleic acid probes and primers of the present disclosure hybridize under stringent conditions to a target DNA sequence. In general, any conventional nucleic acid hybridization or amplification method can be used to identify the presence of DNA from a fad-3c sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the disclosure may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.50 mM to about 02.00 mM $MgCl_2$ at temperatures of about 50° C. to about 75° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In one exemplary embodiment, a nucleic acid of the present disclosure will specifically hybridize to one or more of the primers (or amplicons or other sequences) exemplified or suggested herein, including complements and fragments thereof, under high stringency conditions. In one aspect of the present disclosure, a marker nucleic acid molecule of the present disclosure has the nucleic acid sequence as set forth herein in one of the exemplified sequences, or complements and/or fragments thereof.

In another aspect of the present disclosure, a marker nucleic acid molecule of the present disclosure shares between 80% and 100% or 90% and 100% sequence identity with such nucleic acid sequences. In a further aspect of the present disclosure, a marker nucleic acid molecule of the present disclosure shares between 95%, 96%, 97%, 98%, and/or 99% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize primarily to, and with a high preference for, their target nucleic-acid sequences, thereby allowing the primer pair to bind and, preferably, produce a unique amplicon.

The term "specific for (a target sequence)" indicates that a probe or primer hybridizes, under stringent hybridization conditions, primarily to, and with a high preference for, the nucleic acid sequence in a sample comprising the target sequence.

As used herein, "amplified DNA" or "amplicon" refers to the product of nucleic-acid amplification of a target nucleic acid sequence that is part of a nucleic acid template. For example, to determine whether the canola plant resulting from a sexual cross contains a SNP of interest as disclosed herein. DNA extracted from a canola plant tissue sample may be subjected to a nucleic acid amplification method using a primer pair that includes a primer derived from an upstream or downstream sequence in the genome of the canola plant adjacent to the SNP site and a second primer derived from the other end of the upstream or downstream sequence in the genome of the canola plant adjacent to the SNP site thereby producing an amplicon that is diagnostic for the presence of the SNP. The amplicon is of a length and has a sequence that is also diagnostic for the wild type or mutatedgene. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). A member of a primer pair derived from the plant genomic sequence may be located a distance from the SNP sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including PCR. A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of the present disclosure. The sequence of a fad-3c SNP can be verified by amplifying such sequences using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where a DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

TaqMan® PCR is a method of detecting and quantifying the presence of a DNA sequence. Briefly, a FRET oligonucleotide probe is designed that it overlaps a SNP of interest. The FRET probe and PCR primers (at least one upstream and at least one downstream of the SNP of interest) are cycled in the presence of a thermostable polymerase and dNTPs.

Following amplification, allelic discrimination analysis (using the TaqMan® hydrolysis probe described above), may be performed for determining the presence of a SNP of interest and the zygosity of the sample. During allelic discrimination analysis, two different hybridization probes (one probe including a nucleotide complementary to the SNP sequence and the other probe having a nucleotide complementary to the wild type sequence) are hybridized to the amplicon and digested, thereby releasing the quencher moieties from the probe due to the 5' exonuclease activity of the taq polymerase and resulting in fluorescence. A comparison of the relative fluorescence of a probe specific for the wild type gene versus a probe specific for the SNP provides an indication of the presence and zygosity of the SNP of interest.

All patents, patent applications, provisional applications, and publications referred to or cited herein are incorporated by reference in their entirety to the extent they are not inconsistent with the explicit teachings of this specification.

The following examples are included to illustrate procedures for practicing the disclosure and to demonstrate certain preferred embodiments of the disclosure. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the disclosure. Unless otherwise indicated, all percentages are by weight and all solvent mixture proportions are by volume unless otherwise noted.

The following abbreviations are used unless otherwise indicated.
bp base pair
° C. degrees Celcius
DNA deoxyribonucleic acid
FRET fluorescence resonance energy transfer
DIG digoxigenin
EDTA ethylenediaminetetraacetic acid
kb kilobase
μg microgram
μL microliter
mL milliliter
M molar mass
OLP overlapping probe
PCR polymerase chain reaction
PTU plant transcription unit
SDS sodium dodecyl sulfate
SNP single nucleotide polymorphism
SOP standard operating procedure
SSC a buffer solution containing a mixture of sodium chloride and sodium citrate, pH 7.0
TBE a buffer solution containing a mixture of Tris base, boric acid and EDTA, pH 8.3
V volts

EXAMPLES

Example 1: FAD-3c End Point TAQMAN® Assay

An end-point TaqMan® assay was developed to detect the fad-3c single nucleotide polymorphism mutation and to determine zygosity status of canola plants containing the fad-3c gene mutation in breeding populations. Two primers were designed to bind highly conserved DNA sequences located on exon 6 and 7 of the fad-3c gene. These primers amplified a 154 bpDNA fragment which spanned across the fad-s3c single nucleotide polymorphism in mutated and un-mutated canola plants. The fad-3c mutation in canola is described by Hu et al. (2006) and located in the exon 6 and intron 6 splice site junction of the gene (FIG. 1). Two TaqMan® minor groove binding non-fluorescent quencher (MGBNFQ) probes were designed with FAM and VIC as reporter dyes to detect the presence of the wild type fad-3c gene and the mutated fad-3c gene (which consists of a single nucleotide polymorphism, SNP), respectively. These two probes were designed with special considerations to avoid a neighboring polymorphism located on the intron 6 and in close proximity to the fad-3c single nucleotide polymorphism (FIG. 1). Avoiding the second polymorphism resulted in increased specificity of the probes for detection of the fad-3c mutant plants. The TaqMan® detection method for canola plants containing the fad-3c SNP was tested against canola variety "NEX 828" (containing the fad-3c SNP), control canola variety "Quantum" (does not contain the fad-3c SNP) and a DNA sample isolated from plants known to be heterozygous for the fad-3c SNP. The end-point TaqMan® assay was used to determine the presence of the fad-3c SNP and also to determine the zygosity of the plants being tested in a high throughput application, for example 96 and 384 well plate formats.

Example 1.1: gDNA Isolation

Genomic DNA (gDNA) samples of 156 different canola plants containing the fad-3c mutation and control canola plants were tested in this study. Genomic DNA was extracted using modified Qiagen MagAttract plant DNA kit (Qiagen, Valencia, Calif.). Fresh canola leaf discs, 4 per sample, were used for gDNA extraction. The gDNA was quantified with the Pico Green method according to vendor's instructions (Molecular Probes, Eugene, Oreg.). Samples were diluted with DNase-free water resulting in a concentration of 5 ng/µL for the purpose of this study.

Example 1.2: TaqMan® Assay and Results

Specific TaqMan® primers and probes were designed for use in a TaqMan® end point assay. These primers and probes were designed to amplify and detect the region of the fad-3c gene comprising the SNP of interest. These reagents can be used with the conditions listed below to detect the mutated fad-3c gene within canola plants. Table 1 lists the primer and probe sequences that were developed specifically for the detection of the fad-3c SNP in canola plants.

TABLE 1

Taqman PCR Primers and Probes

| SEQ ID NO: | Name | Description | Sequence |
|---|---|---|---|
| SEQ ID NO: 2 | D-CL-FAD3c-F | Forward primer | ACGATGATAAGCTGCCTTGGT |
| SEQ ID NO: 3 | D-CL-FAD3c-R | Reverse primer | CAAGTACCTCAACAACCCTTTGGTCAACAGTTGTTAATCCTCCACGT |
| SEQ ID NO: 4 | D-CL-FAD3c-FAM | Probe to detect fad-3c mutant | 6FAM-CAGAGGCAAGATAAGT-MGB |
| SEQ ID NO: 5 | D-CL-FAD3c-VIC | Probe to detect fad-3c wild type | VIC-ACAGAGGCAAGGTAAGT-MGB |

The PCR reaction mixtures for amplification are as follows: 1× TaqMan® GTExpress Master Mix, 0.9 µM forward primer (SEQ ID NO:2), 0.9 µM reverse primer (SEQ ID NO:3), 0.2 µM FAD-3C mutant probe (SEQ ID NO:4), 0.2 µM wild type Probe (SEQ ID NO:5), 15 ng gDNA in a total reaction of 6 µl. The reaction mixture was amplified using the following thermal cycling conditions: initial two steps of 50° C. for 2 min and 95° C. for 30 sec; followed by 40 cycles of 3 seconds at 95° C. and 30 seconds at 62° C. The reactions were then kept at 10° C. until being removed from the thermal cycler. PCR thermal cycling can be performed ether using ABI-Applied Biosystems 7900 HT real time PCR system or Applied Biosystems Verity thermal Cyclers (Life Technologies, Carlsbad, Calif.). The sample plates consisted of control DNA from canola plants that were homozygous for the fad-3c mutant ("NEX 828"), heterozygous for the fad-3c mutant, or homozygous for the fad-3c wild type ("Quantum"). In addition, a no template control which did not contain DNA was included. After amplification the end point florescent signals (VIC and FAM) were read using Applied Biosystems 7900 HT real time PCR system according to the allelic discrimination plate reading procedure as described by the manufacturer. The data was then analyzed using SDS 2.4 software (Life Technologies, Carlsbad, Calif.) to determine the relative fluorescence of each sample (FIG. 2).

The TaqMan® detection method for the fac-3c mutation in canola was tested against known homozygous, hemizygous, and wildtype samples. An analysis of the florescence produced from each probe (of a sample's reaction), with the florescence produced by the probes of the controls, aides in determining the zygosity of each sample. This assay demonstrated high specificity for the detection of the fad-3c mutation and wildtype single nucleotide polymorphism in canola and did not produce or amplify any detectable false-positive results from the controls. The event specific primers and probes can be used for the detection of the fad-3c mutant and fad-3c wild type gene in canola and these conditions and reagents are applicable for zygosity assays.

What is claimed is:

1. A method for determining zygosity of a canola plant comprising a fad-3c gene, said method comprising:
   obtaining a sample of genomic DNA from a canola plant;
   hybridizing the sample of genomic DNA with a first primer and a second primer, wherein said first primer and second primer comprise SEQ ID NO: 2 and SEQ ID NO: 3;
   subjecting said sample to polymerase chain reaction (PCR) conditions, wherein an amplicon is produced;
   allowing each of a first probe and a second probe to hybridize to the amplicon for a period of time and at a temperature between 50-70 degrees Celsius, wherein said first probe and second probe comprise SEQ ID NO: 5 and SEQ ID NO: 4, wherein each of said first probe and second probe is labeled with a fluorescent dye and a quencher;
   increasing said temperature after the period of time;
   measuring florescence of the first probe, the second probe, or a combination thereof; and
   determining zygosity of said canola plant.

2. The method of claim 1, wherein said amplicons consist of 91-154 base pairs.

3. The method of claim 1, wherein the sample of genomic DNA comprises a mutated fad-3c sequence having a single nucleotide polymorphism, wherein said single nucleotide polymorphism consists of a G-to-A polymorphism.

4. The method of claim 3, wherein the sample of genomic DNA further comprises a wild-type fad-3c sequence.

5. The method of claim 1, wherein said method is used for breeding introgression verification of cross-bred canola plants.

6. The method of claim 1, wherein said first probe comprises FAM as said fluorescent dye at the 5' end of said first probe and a MGB quencher on the 3' end of said first probe.

7. The method of claim 1, wherein said second probe is labeled with VIC at the 5' end of said second probe and a MGB quencher at the 3' end of said second probe.

8. The method of claim 1, wherein said second probe comprises SEQ ID NO:4.

9. The method of claim 1, wherein florescence results of said method are analyzed directly in a plate reader.

10. The method of claim 1, wherein said DNA sample is obtained from a canola plant in a field.

11. The method of claim 1, wherein the step of increasing comprising increasing said temperature in substantially uniform increments of temperature per period of time.

12. The method of claim 1, wherein said florescence produced by each of said first probe and second probe during the step of increasing is measured during each increment of the step of increasing said temperature.

13. The method of claim 1, wherein said first probe hybridizes to a region of a mutated fad-3c sequence having a single nucleotide polymorphism (SNP) and said second probe hybridizes to a region of a wild-type fad-3c sequence.

* * * * *